(12) United States Patent
Chang

(10) Patent No.: US 11,141,372 B2
(45) Date of Patent: Oct. 12, 2021

(54) HAIR DYE REMOVING COMPOSITION AND PREPARATION METHOD THEREFOR

(71) Applicant: Hye Young Chang, Daegu (KR)

(72) Inventor: Hye Young Chang, Daegu (KR)

( * ) Notice: Subject to any disclaimer, the term of this patent is extended or adjusted under 35 U.S.C. 154(b) by 0 days.

(21) Appl. No.: 17/047,679

(22) PCT Filed: Dec. 28, 2018

(86) PCT No.: PCT/KR2018/016920
§ 371 (c)(1),
(2) Date: Oct. 14, 2020

(87) PCT Pub. No.: WO2020/036269
PCT Pub. Date: Feb. 20, 2020

(65) Prior Publication Data
US 2021/0154131 A1    May 27, 2021

(30) Foreign Application Priority Data

Aug. 13, 2018 (KR) .................. 10-2018-0094367

(51) Int. Cl.
*A61K 8/9789* (2017.01)
*A61K 8/9794* (2017.01)
*A61Q 5/08* (2006.01)

(52) U.S. Cl.
CPC .......... *A61K 8/9789* (2017.08); *A61K 8/9794* (2017.08); *A61Q 5/08* (2013.01)

(58) Field of Classification Search
None
See application file for complete search history.

(56) References Cited

U.S. PATENT DOCUMENTS

2017/0312207 A1* 11/2017 Saeki .................. A61K 8/06

FOREIGN PATENT DOCUMENTS

| CN | 101340891 A | 1/2009 |
|---|---|---|
| KR | 100960054 B1 | 5/2010 |
| KR | 2011-0012719 A | 2/2011 |
| KR | 2011-0023161 A | 3/2011 |
| KR | 101129693 B1 | 3/2012 |
| KR | 2014-0126160 A | 10/2014 |

OTHER PUBLICATIONS

Benefits and techniques of vacuum mixing; retrieved online [Feb. 27, 2021]; retrieved from www.mixers.com>insights>mti_35 (Year: 2021).*

* cited by examiner

*Primary Examiner* — Nannette Holloman
(74) *Attorney, Agent, or Firm* — K&L Gates LLP

(57) ABSTRACT

The present invention relates to a hair dye removing composition. The present invention provides: a hair dye removing composition, which contains one or more extracts selected from the group consisting of a squeezed lemon juice, a *Gardenia jasminoides* extract, a black rice extract and a mugwort extract, and thus does not use chemical surfactants, has low skin irritation, and can sooth the skin while effectively removing hair dye from the skin or the hair; and a preparation method therefor.

13 Claims, 4 Drawing Sheets

[FIG. 1]
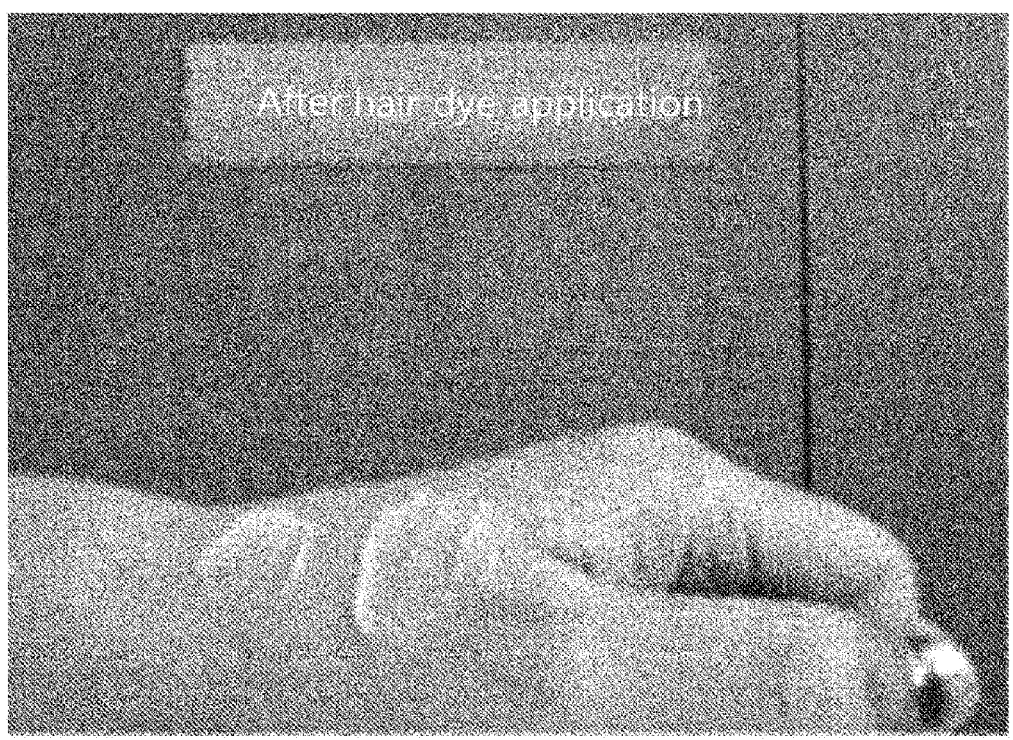

[FIG. 2]
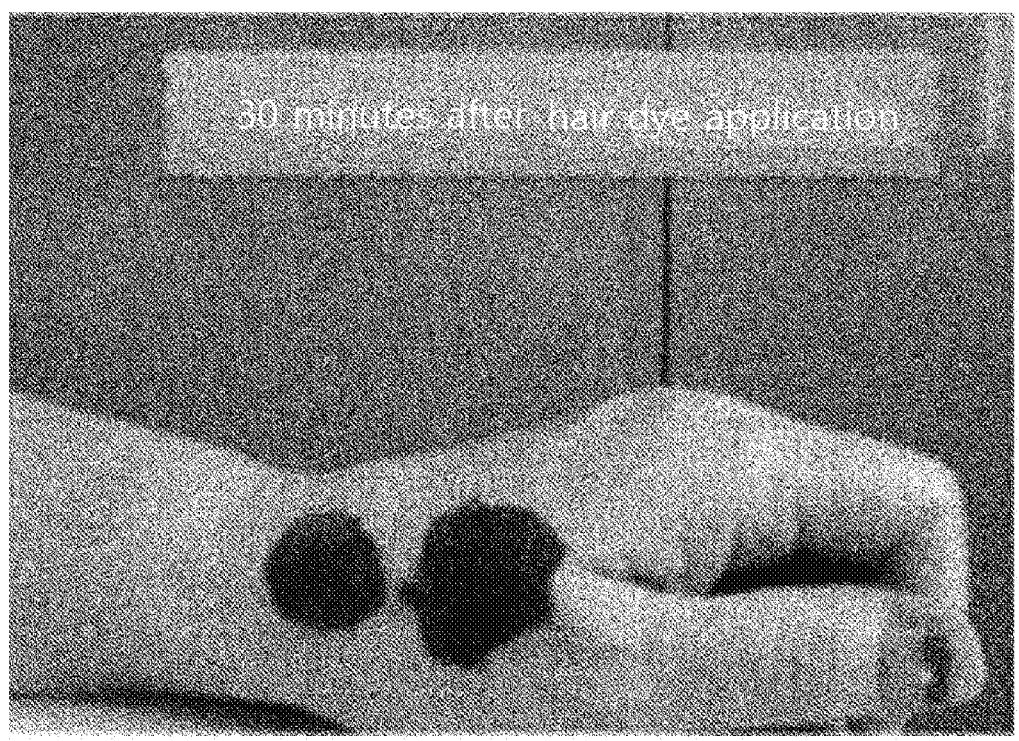

[FIG. 3]
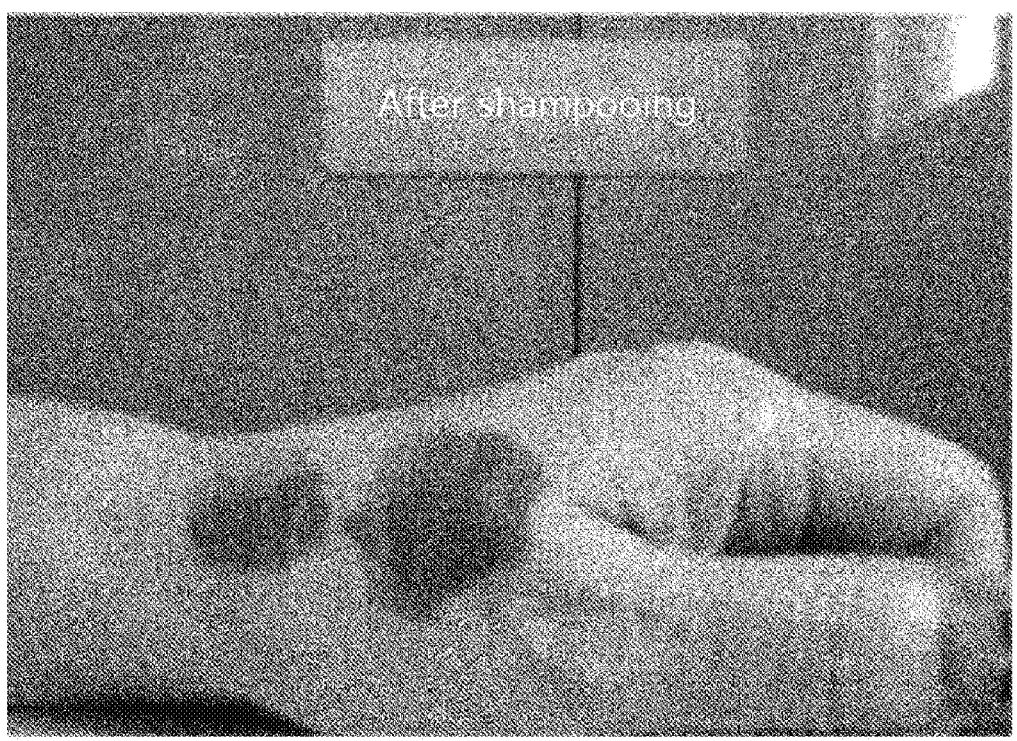

[FIG. 4]
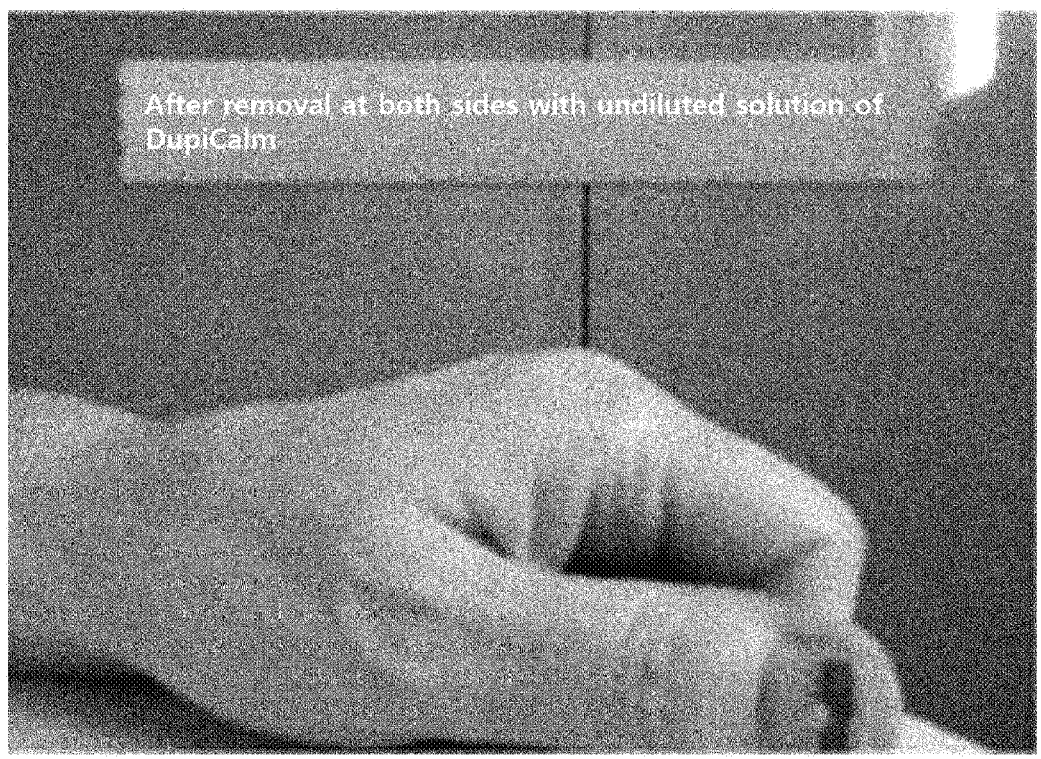

HAIR DYE REMOVING COMPOSITION AND PREPARATION METHOD THEREFOR

TECHNICAL FIELD

The present invention relates to a hair dye removal composition and a method of preparing the same.

BACKGROUND ART

Dyeing is a process of changing hair color variously using a hair dye and may be performed by evenly applying a hair dye on hair, allowing hair to stand for a certain period of time, and then rinsing the hair dye.

In general, the hair dye used in dyeing includes components such as p-phenylenediamine and hydrogen peroxide. However, when the components are brought into contact with skin for a long time, skin allergy, inflammation, DNA damage, corneal damage, hives, rash, erythema, vitiligo, scalp discoloration, or the like may occur. Thus, conventionally, the hair dye was always rinsed with a shampoo and a rinse after dyeing, thereby preventing the above problems.

Meanwhile, since a main purpose of the shampoo and the rinse is to remove sweat, sebum, dust, and the like of a scalp, the hair dye attached to the scalp or hair was not sufficiently removed. Accordingly, the hair dye remained on the scalp or hair to cause the diseases described above. In addition, since a conventional shampoo includes a chemical surfactant such as sodium lauryl sulfate, sodium laureth sulfate, ammonium lauryl sulfate, and ammonium laureth sulfate, skin irritation was rather caused.

In order to solve the problems, recently, a hair dye removal composition using components derived from nature and the like has been developed. As an example, Korean Patent Registration No. 10-1129693 discloses a hair cleaning rinse composition for dyeing which is a mixed solution in which 16 to 28 mL of a herb extract and 0.1 to 2 g of alum are mixed per 1000 mL of vinegar, wherein the herb extract is extracted from one or more herbs selected from peppermint, jasmine, chamomile, lemongrass, rose flower, lavender, and rosemary.

However, like the above registered patent, when a material derived from nature was used, a hair dye removal effect was insignificant and side effects such as skin inflammation or damage occurred constantly. In addition, a large amount of an acid component was used for removing the hair dye, but which only irritates the skin and is insufficient for the hair dye removal effect.

Accordingly, development of a hair dye removal composition which does not include a chemical surfactant so as to be less irritating to the skin and effectively removes a hair dye attached to the skin or hair so as to solve problems such as erythema or skin problems which occur due to the hair dye remaining on the skin or hair, is demanded.

DISCLOSURE

Technical Problem

An object of the present invention is to provide a hair dye removal composition which does not use a chemical surfactant, is less irritating to the skin, may effectively remove a hair dye attached to the skin or hair, and may prevent skin diseases such as erythema and skin problems.

Another object of the present invention is to provide a method of preparing a hair dye removal composition which does not use a chemical surfactant, is less irritating to the skin, may effectively remove a hair dye attached to the skin or hair, and may prevent skin diseases such as erythema and skin problems.

The object of the present invention is not limited to the technical problems described above, and another technical problem may be derived from the following description.

Technical Solution

In one general aspect, a hair dye removal composition includes lemon juice; and one or more extracts selected from the group consisting of a *gardenia* extract, a black rice extract, and a mugwort extract.

The hair dye removal composition may include 10 to 30 parts by weight of the *gardenia* extract with respect to 100 parts by weight of the lemon juice.

The hair dye removal composition may include 10 to 30 parts by weight of the *gardenia* extract, 0.5 to 15 parts by weight of the black rice extract, and 0.1 to 10 parts by weight of the mugwort extract with respect to 100 parts by weight of the lemon juice.

An extraction solvent of the *gardenia* extract, the black rice extract, and the mugwort extract may be water or a lemon juice solution.

In another general aspect, a method of preparing a hair dye removal composition includes: (a) preparing lemon juice; (b) preparing one or more extracts selected from the group consisting of a *gardenia* extract, a black rice extract, and a mugwort extract; and (c) mixing the lemon juice with the one or more extracts selected from the group consisting of the *gardenia* extract, the black rice extract, and the mugwort extract to prepare a mixed solution.

The method of preparing a hair dye removal composition may further include (d) stirring the mixed solution in vacuum.

The method of preparing a hair dye removal composition may further include (e) stirring the mixed solution stirred in vacuum to be stabilized, wherein in (e) stirring the mixed solution stirred in vacuum to be stabilized, the stirring is performed at a lower rotation speed for a longer time than in (d) stirring the mixed solution in vacuum.

The *gardenia* extract may be extracted from *gardenia* using water or a lemon juice solution as an extraction solvent.

The black rice extract may be extracted using water or the lemon juice solution as the extraction solvent after heat-treating black rice with hot steam.

The mugwort extract may be extracted using water or the lemon juice solution as the extraction solvent after pulverizing mugwort.

The *gardenia* extract may be hydrothermally extracted from a mixture of 2 to 10 parts by weight of *gardenia* with respect to 100 parts by weight of water.

The black rice extract may be extracted from a mixture of 10 to 50 parts by weight of black rice which has been heat-treated with hot steam with respect to 100 parts by weight of water or the lemon juice solution.

The mugwort extract may be extracted from a mixture of 10 to 70 parts by weight of dried and crushed mugwort with respect to 100 parts by weight of water or the lemon juice solution.

Advantageous Effects

The hair dye removal composition of the present invention includes lemon juice, a *gardenia* extract, a black rice extract, and a mugwort extract, thereby having effects of not using a chemical surfactant, being less irritating to the skin, effectively removing the hair dye attached to the skin or hair, and soothing the skin.

In particular, the hair dye composition of the present invention includes the lemon juice, the *gardenia* extract, the black rice extract, and the mugwort extract at specific contents (wt %), thereby having more improved hair dye removal efficiency.

In addition, according to the method of preparing a hair dye removal composition of the present invention, the lemon juice, the *gardenia* extract, the black rice extract, and the mugwort extract are prepared, respectively, and then mixed, and the mixture is stirred in vacuum at a high speed, homogenized, and stabilized, thereby allowing preparation of the hair dye removal composition which does not use a chemical surfactant, is less irritating to the skin, may effectively remove the hair dye attached to the skin or hair, and has a skin soothing effect.

In particular, in the present invention, a hair dye removal composition is prepared using a hydrothermal extract of *gardenia* as the *gardenia* extract and a lemon solution as the extraction solvent of the black rice extract and the mugwort extract, thereby further improving a hair dye removal effect.

DESCRIPTION OF DRAWINGS

FIG. 1 is a drawing illustrating an appearance in which a hair dye used in Experimental Example 1 was applied to a hand.

FIG. 2 is a drawing illustrating an appearance in which 30 minutes had passed since the hair dye was applied FIG. 3 is a drawing illustrating an appearance after cleansing the hair dye with shampoo.

FIG. 4 is a drawing illustrating an appearance after cleansing the hair dye with a hair dye removal composition of Example 1.

BEST MODE

Hereinafter, exemplary embodiments of the present invention will be described in detail with reference to the accompanying drawings so that the present invention can be easily practiced by those skilled in the art to which the present invention pertains. However, the present invention may be implemented in various different forms and is not limited to the embodiments provided in the present description. In the drawings, parts which are not related to the description were omitted for clear description of the present invention.

Terms or words used in the specification and claims of the present invention are not to be construed as a general or dictionary meaning but are to be construed as meaning and concepts meeting the technical ideas of the present invention based on a principle that the inventors can appropriately define the concepts of terms in order to describe their own inventions in best mode.

Throughout the specification of the present invention, unless otherwise stated explicitly, "comprising" any components will be understood to imply the inclusion of other components rather than the exclusion of other components.

Throughout the specification of the present invention, "A and/or B" means A or B, or A and B.

Throughout the specification of the present invention, an "extract" has a wide range of concepts including all materials obtained by pulling out components of a natural material, regardless of an extraction method, an extraction solvent, an extracted component, or an extract form, and also including all materials which may be obtained by extracting a material obtained by pulling out components of a natural material and then processing or treating the material.

Throughout the specification of the present invention, "skin" includes a scalp and refers to a coated film covering a body surface of an animal.

Throughout the specification of the present invention, a "lemon juice solution" may refer to a juice, a juice solution, or an extract obtained by juicing a lemon. The lemon juice solution of the present invention may be the same as the lemon juice of the present invention, but is not limited thereto.

Throughout the specification of the present invention, "(a) preparing lemon juice" may be simply referred to as "step (a)".

Throughout the specification of the present invention, "(b) preparing one or more extracts selected from the group consisting of a *gardenia* extract, a black rice extract, and a mugwort extract" may be simply referred to as "step (b)".

Throughout the specification of the present invention, "(c) mixing the lemon juice with one or more extracts selected from the group consisting of the *gardenia* extract, the black rice extract, and the mugwort extract to prepare a mixed solution" may be simply referred to as "step (c)".

Throughout the specification of the present invention, "(d) stirring the mixed solution in vacuum" may be simply referred to as "step (d)".

Throughout the specification of the present invention, "(e) stirring the mixed solution stirred in vacuum to be stabilized" may be simply referred to as "step (e)".

Hereinafter, the present invention will be described in detail, but the present invention is not limited thereto.

In the present invention, a hair dye removal composition is provided.

In an exemplary embodiment of the present invention, a hair dye removal composition including lemon juice; and one or more extracts selected from the group consisting of a *gardenia* extract, a black rice extract, and a mugwort extract is provided. The hair dye removal composition of the present exemplary embodiment does not include a chemical surfactant, is less irritating to the skin, may effectively remove the hair dye attached to the skin or hair, and may prevent skin diseases such as erythema and skin problems.

The hair dye removal composition of the present exemplary embodiment includes lemon juice, and one or more extracts selected from the group consisting of a *gardenia* extract, a black rice extract, and a mugwort extract.

Preferably, the hair dye removal composition of the present exemplary embodiment may include the lemon juice and the *gardenia* extract.

More preferably, the hair dye removal composition of the present exemplary embodiment may include the lemon juice, the *gardenia* extract, and one or more extracts selected from the group consisting of the black rice extract and the mugwort extract.

Most preferably, the hair dye removal composition of the present exemplary embodiment may include the lemon juice, the *gardenia* extract, the black rice extract, and the mugwort extract. That is, when the hair dye removal composition of the present exemplary embodiment includes the lemon juice, the *gardenia* extract, the black rice extract, and the mugwort extract, the composition may be less irritating to the skin and have remarkably excellent hair dye removal efficiency.

The lemon juice is obtained by juicing a lemon, and may refer to all forms of materials which may be obtained by juicing a lemon by all known methods. For example, the lemon juice may be prepared by washing a lemon, juicing the lemon, removing solids by filtering, and then performing centrifugation at a high speed for homogenization.

The juicing may refer to heat treatment juicing or compression juicing. Preferably, in the present exemplary embodiment, in order to effectively extract an antioxidant, an antibacterial substance, and the like contained in a lemon, compression juicing may be performed rather than heat treatment juicing.

The *gardenia* extract may be extracted by washing *gardenia* and then using water or a lemon juice solution as an extraction solvent. Preferably, the *gardenia* extract of the present exemplary embodiment may be obtained by hydrothermal extraction from *gardenia*, but is not limited thereto. For example, the *gardenia* extract of the present exemplary embodiment may be obtained by mixing 2 to 10 parts by weight of *gardenia* with respect to 100 parts by weight of water and then performing hydrothermal extraction from the mixture.

The hydrothermal extraction is extraction by heating water and may refer to extraction by heating water to about 70 to 100° C., but preferably, may refer to extraction by boiling water.

The hair dye removal composition of the present exemplary embodiment may include 10 to 30 parts by weight of the *gardenia* extract with respect to 100 parts by weight of the lemon juice.

When the hair dye removal composition of the present exemplary embodiment includes 10 to 30 parts by weight of the *gardenia* extract with respect to 100 parts by weight of the lemon juice, the hair dye removal composition may have a low skin irritation degree and excellent hair dye removal efficiency. That is, when the lemon juice and the *gardenia* extract are included at the composition ratio, the hair dye removal effect, the skin soothing effect, and the skin inflammation relief effect of the hair dye removal composition may be the best.

However, when an excessive amount of the *gardenia* extract out of the range of the composition ratio is included with respect to the lemon juice, the skin irritation degree may be somewhat high, and thus, it is preferred to satisfy the range; however, considering the hair dye removal effect, the case in which an excessive amount of the *gardenia* extract out of the range of the composition ratio is included with respect to the lemon juice is not excluded from the present invention.

The black rice extract is obtained by extraction from black rice with an extraction solvent, and the extraction solvent may be water or a lemon juice solution, preferably a lemon juice solution. In particular, the black rice extract of the present exemplary embodiment is obtained using an acidic lemon juice solution as the extraction solvent, not a common solvent such as water or ethanol, thereby significantly improving the hair dye removal efficiency while being less irritating to the skin.

For example, the black rice extract of the present exemplary embodiment may be prepared by heat-treating the black rice extract with hot steam for 2 to 30 minutes, mixing 10 to 50 parts by weight of the black rice with respect to 100 parts by weight of water or the lemon juice solution, and then stirring the mixture at 10 to 80° C. for 10 minutes to 10 hours. The thus-prepared product may be used as the black rice extract, or only a liquid material obtained by removing solids therefrom may be used as the black rice extract. The hot steam may be water vapor formed by heating water at 100° C. or higher, but is not limited thereto.

The hair dye removal composition of the present exemplary embodiment may include 0.5 to 15 parts by weight of the black rice extract with respect to 100 parts by weight of the lemon juice. When the hair dye removal composition of the present exemplary embodiment includes 0.5 to 15 parts by weight of the black rice extract with respect to 100 parts by weight of the lemon juice, the hair dye removal composition may have a low skin irritation degree and better hair dye removal efficiency.

In addition, non-restrictively, when the hair dye removal composition of the present exemplary embodiment includes the black rice extract within the range described above, the hair dye removal composition has increased compatibility between each component so as to be formed as a transparent formulation without occurrence of an aggregate, which is thus preferred.

The mugwort extract refers to all forms of materials extracted from mugwort which is dried and crushed with the extraction solvent, and the extraction solvent may be water or the lemon juice solution, preferably the lemon juice solution. In particular, the mugwort extract of the present exemplary embodiment is obtained using an acidic lemon juice solution as the extraction solvent, not a common solvent such as water or ethanol, thereby significantly improving the hair dye removal efficiency while being less irritating to the skin.

For example, the mugwort extract of the present exemplary embodiment may be prepared by adding 10 to 70 parts by weight of dried and crushed mugwort with respect to 100 parts by weight of water or the lemon juice solution, and stirring the mixture at 10 to 80° C. for 10 minutes to 10 hours. The thus-prepared product may be used as the mugwort extract, or only a liquid material obtained by removing solids therefrom may be used as the mugwort extract.

The hair dye removal composition of the present exemplary embodiment may include 0.1 to 10 parts by weight of the mugwort extract with respect to 100 parts by weight of the lemon juice. When the hair dye removal composition includes 0.1 to 10 parts by weight of the mugwort extract with respect to 100 parts by weight of the lemon juice, the hair dye removal composition is less irritating to the skin, has an excellent hair dye removal effect, smells good, and has increased compatibility between each component so as to have excellent transparency even in the case of long term storage, which is thus preferred.

The hair dye removal composition of the present exemplary embodiment includes lemon juice, and one or more extracts selected from the group consisting of a *gardenia* extract, a black rice extract, and a mugwort extract.

Preferably, the hair dye removal composition of the present exemplary embodiment may include the lemon juice and the *gardenia* extract, and 10 to 30 parts by weight of the *gardenia* extract with respect to 100 parts by weight of the lemon juice.

More preferably, the hair dye removal composition of the present exemplary embodiment may include the lemon juice, the *gardenia* extract, and one or more extracts selected from the group consisting of the black rice extract and the mugwort extract, and include 10 to 30 parts by weight of the *gardenia* extract and 0.5 to 15 parts by weight of one or more extracts selected from the group consisting of the black rice extract and the mugwort extract with respect to 100 parts by weight of the lemon juice.

Most preferably, the hair dye removal composition of the present exemplary embodiment may include the lemon juice, the *gardenia* extract, the black rice extract, and the mugwort extract, and may include 10 to 30 parts by weight of the *gardenia* extract, 0.5 to 15 parts by weight of the black rice extract, and 0.1 to 10 parts by weight of the mugwort extract with respect to 100 parts by weight of the lemon juice.

In addition, in the present invention, a method of preparing a hair dye removal composition is provided.

In another exemplary embodiment of the present invention, a method of preparing a hair dye removal composition including: (a) preparing lemon juice (b) preparing one or more extracts selected from the group consisting of a *gardenia* extract, a black rice extract, and a mugwort extract and (c) mixing the lemon juice with the one or more extracts selected from the group consisting of the *gardenia* extract, the black rice extract, and the mugwort extract to prepare a mixed solution, is provided.

The hair dye removal composition prepared by the present exemplary embodiment does not include a chemical surfactant, is less irritating to the skin, may effectively remove the hair dye attached to the skin or hair, and may prevent skin diseases such as erythema and skin problems.

In addition, the hair dye removal composition of the present exemplary embodiment includes the lemon juice and one or more extracts selected from the group consisting of the *gardenia* extract, the black rice extract, and the mugwort extract.

Preferably, the hair dye removal composition of the present exemplary embodiment may include the lemon juice and the *gardenia* extract.

More preferably, the hair dye removal composition of the present exemplary embodiment may include the lemon juice, the *gardenia* extract, and one or more extracts selected from the group consisting of the black rice extract and the mugwort extract.

Most preferably, the hair dye removal composition of the present exemplary embodiment may include the lemon juice, the *gardenia* extract, the black rice extract, and the mugwort extract. When the hair dye removal composition of the present exemplary embodiment includes the lemon juice, the *gardenia* extract, the black rice extract, and the mugwort extract, the composition may be less irritating to the skin and have remarkably excellent hair dye removal efficiency.

(a) Step of preparing lemon juice

In step (a) of the present exemplary embodiment, lemon is washed, compressed, and juiced to prepare the lemon juice. For example, in step (a) of the present exemplary embodiment, lemon is washed and compressed to separate juice, which is then filtered and centrifuged at a high speed to obtain only a liquid material, thereby preparing the lemon juice.

(b) Step of preparing one or more extracts selected from the group consisting of a *Gardenia* extract, a black rice extract, and a mugwort extract The *gardenia* extract of the present exemplary embodiment may be prepared by washing *gardenia* and then extracting using water or a lemon juice solution as an extraction solvent. Preferably, the *gardenia* extract of the present exemplary embodiment may be obtained by hydrothermal extraction from *gardenia*, but is not limited thereto. For example, the *gardenia* extract of the present exemplary embodiment may be obtained by mixing 2 to 10 parts by weight of *gardenia* with respect to 100 parts by weight of water and then performing hydrothermal extraction from the mixture. The thus-prepared product may be used as the *gardenia* extract, or only a liquid material obtained by removing solids therefrom may be used as the *gardenia* extract.

The black rice extract of the present exemplary embodiment may be extracted using water or the lemon juice solution as the extraction solvent after heat-treating the black rice with hot steam. For example, the black rice extract of the present exemplary embodiment may be prepared by heat-treating the black rice extract with hot steam for 2 to 30 minutes, mixing 10 to 50 parts by weight of the black rice with respect to 100 parts by weight water or the lemon juice solution, and then stirring the mixture at 10 to 80° C. for 10 minutes to 10 hours. The thus-prepared product may be used as the black rice extract, or only a liquid material obtained by removing solids therefrom may be used as the black rice extract.

Preferably, the extraction solvent may be the lemon juice solution, and when the lemon juice solution is used as the extraction solvent, the composition may be less irritating to the skin and have significantly improved hair dye removal efficiency.

The mugwort extract of the present exemplary embodiment may be prepared by drying and crushing mugwort and performing extraction with the extraction solvent. For example, the mugwort extract of the present exemplary embodiment may be prepared by adding 10 to 70 parts by weight of dried and crushed mugwort with respect to 100 parts by weight of water or the lemon juice solution, and stirring the mixture at 10 to 80° C. for 10 minutes to 10 hours. The thus-prepared product may be used as the mugwort extract, or only a liquid material obtained by removing solids therefrom may be used as the mugwort extract.

Preferably, the extraction solvent may be the lemon juice solution, and when the lemon juice solution is used as the extraction solvent, the composition may be less irritating to the skin and have significantly improved hair dye removal efficiency.

The pulverization of mugwort may be performed by crushing directly by a person using a mortar or crushing with a machine such as a mixer.

(c) Step of mixing the lemon juice with one or more extracts selected from the group consisting of a *Gardenia* extract, a black rice extract, and a mugwort extract to prepare a mixed solution In step (c) of the present exemplary embodiment, the lemon juice prepared as described above and an extract including one or more selected from the group consisting of the *gardenia* extract, the black rice extract, and the mugwort extract is added into a reactor and mixed, thereby preparing the mixed solution.

In the present exemplary embodiment, (d) stirring the mixed solution in vacuum may be further included.

The mixed solution in which the lemon juice and an extract including one or more selected from the group consisting of the *gardenia* extract, the black rice extract, and the mugwort extract are mixed is stirred in vacuum, thereby making the state of the mixed solution uniform.

The stirring in step (d) may be performed at about 30,000 to 40,000 rpm for 3 to 5 minutes, but is not limited thereto and may be changed as required.

In step (d) of the present exemplary embodiment, in order to prevent oxidation, denaturalization, contamination by a foreign matter of the lemon juice and the extract including one or more selected from the group consisting of the *gardenia* extract, the black rice extract, and the mugwort extract, the stirring may be performed in a closed vacuum state. Accordingly, the characteristics of the hair dye removal effect and the antioxidative effect of the lemon juice solution and one or more extracts selected from the group consisting of the *gardenia* extract, the black rice extract, and the mugwort extract may be maintained.

In addition, since the stirring is performed in vacuum, each component has a uniform composition and does not cause problems such as oxidation, denaturalization, or contamination by air during mixing.

In the present exemplary embodiment, (e) stirring the mixed solution stirred in vacuum according to step (d) to be stabilized may be further included.

In step (e) of the present exemplary embodiment, the mixed solution which has been stirred at a high speed according to step (d) may be stirred at room temperature to be stabilized, thereby preparing the hair dye removal composition. The stirring in step (e) may be performed at 300 to 400 rpm for 1 to 3 hours, but is not limited thereto and may be changed as required.

Step (e) of the present exemplary embodiment is performed in a closed reactor in which contact with air is cut off, thereby minimizing the oxidation, the denaturalization, and the contamination by a foreign matter of the mixed solution. Accordingly, the characteristics of the hair dye removal effect and the antioxidative effect of the lemon juice solution and one or more extracts selected from the group consisting of the *gardenia* extract, the black rice extract, and the mugwort extract may be maintained.

In addition, (e) stirring the mixed solution stirred in vacuum to be stabilized is further included, wherein in (e) stirring the mixed solution stirred in vacuum to be stabilized, the stirring is carried out at a lower rotation speed for a longer time than in (d) stirring the mixed solution in vacuum, thereby stabilizing the formulation of the hair dye removal composition to minimize occurrence of aggregation, precipitation, and the like which may occur during long-term storage.

The method of preparing a hair dye removal composition of the present invention includes all descriptions of the hair dye removal composition.

Hereinafter, by the following Examples, Comparative Example, and Experimental Examples, the hair dye removal composition of the present invention and the method of preparing the same will be described in detail. These Examples are only to illustrate the present invention and are not construed as limiting a scope of the present invention.

Preparation Example

The lemon juice, the *gardenia* extract, the black rice extract, and the mugwort extract were prepared as follows.

(1) Lemon juice: a washed lemon was juiced, the lemon juice was filtered through filter paper to remove solids, and the filtered lemon juice was centrifuged to obtain lemon juice in a transparent liquid state.

(2) *Gardenia* extract: 5 parts by weight of *gardenia* which was washed and cut in half was mixed with respect to 100 parts by weight of water, hydrothermal extraction therefrom was performed, and cooling and filtering were performed, thereby preparing the *gardenia* extract. The hydrothermal extraction was performed by mixing the *gardenia* and water and heating the mixture at 100° C. for 150 minutes.

(3) Black rice extract: black rice was washed, treated with steam at 100° C. for about 10 minutes, and cooled to room temperature. Thereafter, 30 parts by weight of the black rice was mixed with respect to 100 parts by weight of the lemon juice solution, stirring was performed at 1,000 to 1,100 rpm at room temperature for about 1 hour, and then filtering was performed, thereby preparing a red black rice extract.

(4) Mugwort extract: mugwort was dried and crushed using a mortar, 40 parts by weight of the crushed mugwort was mixed with respect to 100 parts by weight of the lemon juice solution, stirring was performed at 600 to 700 rpm at room temperature for about 1 hour, and filtering was performed, thereby preparing the mugwort extract.

The used lemon juice solution was the same as the lemon juice in (1).

EXAMPLES

Examples 1 to 5

The lemon juice and the extract including the *gardenia* extract, the black rice extract, and the mugwort extract prepared according to the Preparation Example were mixed according to the composition in Table 1, thereby preparing the hair dye removal composition.

First, the lemon juice and the extract including the *gardenia* extract, the black rice extract, and the mugwort extract were mixed to prepare a mixed solution, which was then stirred at a speed of 30,000 to 40,000 rpm in vacuum for 3 to 5 minutes. Subsequently, the mixed solution stirred at a high speed was stirred at a speed of about 300 to 400 rpm for 1 to 3 hours to be stabilized, thereby preparing the hair dye removal composition.

TABLE 1

| part by weight | Examples | | | | |
| --- | --- | --- | --- | --- | --- |
|  | 1 | 2 | 3 | 4 | 5 |
| Lemon Juice | 100 | 100 | 100 | 100 | 100 |
| Gardenia extract | 20 | 30 | 25 | 15 | 10 |
| Black rice extract | 5 | — | 5 | — | 7 |
| Mugwort extract | 3 | — | — | 3 | 2 |

Experimental Examples

Experimental Example 1

The hair dye removal compositions of Examples 1 to 5 were used to evaluate a hair dye removal effect, skin irritation, and a smell. About 20 adult women evaluated the following items by a 5-point method, and the average values thereof are shown in Table 2.

(1) Hair dye removal: a specific amount of a dye composed of a hair dye and an oxidant (Loreal Excellence Duo Cream 4) was applied to a human arm and allowed to stand for about 10 minutes, the hair dye removal composition of Examples 1 to 5 was put on cotton wool, and the dye applied to the skin was wiped off using the cotton wool.

A degree of removing the dye was visually evaluated and represented as 1 to 5 points, and the results are shown in Table 2. In Table 2, the hair dye removal effect being closer to 5 points means that the hair dye removal effect is excellent.

(2) Skin irritation: the removal of the hair dye was repeated 5 times and it was evaluated whether erythema occurred on the skin, and the case in which an erythema degree was severe and skin irritation was shown was evaluated as 5 points and the case in which there are almost no erythema and skin irritation was evaluated as 1 point, and the average values thereof are shown in Table 2.

(3) Smell: the smell of the hair dye removal compositions of Examples 1 to 5 was evaluated, and the case in which the smell was good and gave a sense of stability was evaluated as 5 points and the case in which the smell as considered to be disgusting was evaluated as 1 point, and the average values thereof are shown in Table 2.

TABLE 2

| | Examples | | | | |
|---|---|---|---|---|---|
| | 1 | 2 | 3 | 4 | 5 |
| Hair dye removal effect | 4.96 | 4.10 | 4.57 | 4.21 | 4.87 |
| Skin irritation degree | 0.87 | 1.81 | 1.57 | 1.46 | 0.76 |
| Smell | 4.83 | 4.23 | 4.13 | 4.47 | 4.87 |

In Table 2, it is confirmed that when the lemon juice and one or more extracts selected from the group consisting of the *gardenia* extract, black rice extract, and the mugwort extract were included according to the present Examples, the hair dye removal effect was excellent, there was almost no skin irritation, and the smell was good. In particular, in Examples 1 to 5, it was found that when the hair dye removal composition of the present Examples included all of the lemon juice, the *gardenia* extract, the black rice extract, and the mugwort extract, the hair dye removal performance was good, a skin irritation degree was low, and the smell was good.

Further, (1) hair dye removal, (2) skin irritation, and (3) smell tests were performed using a commonly sold shampoo.

The test using a common shampoo was performed by repeating a process of applying a specific amount of a dye composed of a hair dye and an oxidant (Loreal Excellent Duo Cream 4) to a human arm, allowing the dye to stand for about 10 minutes, and cleaning with the shampoo by strong compression for about 5 minutes three times.

As a result, when a common shampoo was used, the hair dye removal effect was evaluated as 2.94, which means that the hair dye was hardly removed. In addition, since it was confirmed that the skin irritation degree was 3.78, which is very irritative, it means that the effect of Examples 1 to 5 according to the present exemplary embodiment is significantly excellent as compared with the case using a common shampoo.

Experimental Example 2

The hair dye removal effect of Example 1 and a common shampoo was evaluated, and the results are shown in FIGS. 1 to 4.

FIG. 1 is a drawing illustrating an appearance in which the hair dye used in Experimental Example 1 was applied to a hand, and FIG. 2 is a drawing illustrating an appearance in which 30 minutes had passed since the dye was applied. In addition, FIG. 3 is a drawing illustrating an appearance after cleaning the hair dye with a shampoo, and FIG. 4 is a drawing illustrating an appearance after cleaning the hair dye with the hair dye removal composition of Example 1.

In FIGS. 1 to 4, it is confirmed that when a commonly sold shampoo was used, the hair dye was insufficiently removed, but as shown in FIG. 4, when the hair dye removal composition of Example 1 according to the present exemplary embodiment was used, the hair dye was completely removed. That is, it is confirmed that the hair dye removal composition according to the present exemplary embodiment had the significantly excellent hair dye removal effect.

As described above, the description of the present invention is for illustration, and those skilled in the art will appreciate that various modifications and alterations may be easily made without departing from the spirit or essential feature of the present invention. Therefore, it should be understood that the exemplary embodiments described above are not restrictive, but illustrative in all aspects. For example, each component described as a singular form may be practiced in a dispersed form, and also, each component described as being dispersed may be practiced in a combined form.

It should be interpreted that the scope of the present invention is defined by the following claims rather than the above-mentioned detailed description and all modifications or alterations deduced from the meaning, the scope, and equivalences of the claims are included in the scope of the present invention.

The invention claimed is:

1. A hair dye removal composition consisting of:
   lemon extract;
   *gardenia* extract; and
   one or more extracts selected from the group consisting of black rice extract and mugwort extract.

2. The hair dye removal composition of claim 1, wherein the hair dye removal composition includes 10 to 30 parts by weight of the *gardenia* extract with respect to 100 parts by weight of the lemon extract.

3. The hair dye removal composition of claim 1, wherein the hair dye removal composition includes 10 to 30 parts by weight of the *gardenia* extract, 0.5 to 15 parts by weight of the black rice extract, and 0.1 to 10 parts by weight of the mugwort extract with respect to 100 parts by weight of the lemon extract.

4. The hair dye removal composition of claim 1, wherein an extraction solvent of the *gardenia* extract, the black rice extract, and the mugwort extract is water or a lemon extract solution.

5. A method of preparing the hair dye removal composition of claim 1, the method comprising:
   (a) preparing lemon extract and *gardenia* extract;
   (b) preparing one or more extracts selected from the group consisting of black rice extract and mugwort extract; and
   (c) mixing the lemon extract, the *gardenia* extract, and the one or more extracts selected from the group consisting of the black rice extract and the mugwort extract to prepare a mixed solution.

6. The method of preparing a hair dye removal composition of claim 5, further comprising: (d) stirring the mixed solution in vacuum.

7. The method of preparing a hair dye removal composition of claim 6, further comprising:
   (e) stirring the mixed solution stirred in vacuum to be stabilized,
   wherein in (e) stirring the mixed solution stirred in vacuum to be stabilized, the stirring is performed at a lower rotation speed for a longer time than in (d) stirring the mixed solution in vacuum.

8. The method of preparing a hair dye removal composition of claim 5, wherein the *gardenia* extract is extracted from *gardenia* using water or a lemon extract solution as an extraction solvent.

9. The method of preparing a hair dye removal composition of claim 5, wherein the black rice extract is extracted using water or a lemon extract solution as an extraction solvent after heat-treating the black rice with hot steam.

10. The method of preparing a hair dye removal composition of claim 5, wherein the mugwort extract is extracted using water or a lemon extract solution as an extraction solvent after pulverizing mugwort.

11. The method of preparing a hair dye removal composition of claim 5, wherein the *gardenia* extract is hydrothermally extracted from a mixture of 2 to 10 parts by weight of *gardenia* with respect to 100 parts by weight of water.

12. The method of preparing a hair dye removal composition of claim 5, wherein the black rice extract is extracted from a mixture of 10 to 50 parts by weight of the black rice which has been heat-treated with hot steam with respect to 100 parts by weight of water or a lemon extract solution.

13. The method of preparing a hair dye removal composition of claim 5, wherein the mugwort extract is extracted from a mixture of 10 to 70 parts by weight of dried and crushed mugwort with respect to 100 parts by weight of water or a lemon extract solution.

* * * * *